United States Patent [19]

Smith

[11] Patent Number: 5,102,903

[45] Date of Patent: Apr. 7, 1992

[54] TREATMENT OF GLAUCOMA AND OCULAR HYPERTENSION WITH PYRAZOLE, PYRROLE AND TRIAZOLE ANGIOTENSIN-II RECEPTOR ANTAGONISTS

[75] Inventor: Ronald D. Smith, Libertyville, Ohio

[73] Assignee: E. I. Du Pont de Nemours and Company, Wilmington, Del.

[21] Appl. No.: 521,553

[22] Filed: May 10, 1990

[51] Int. Cl.$^5$ ............................................ A61K 31/415
[52] U.S. Cl. ..................................... 514/406; 514/913
[58] Field of Search ................ 514/381, 403, 406, 913

[56] References Cited

FOREIGN PATENT DOCUMENTS 871653 3/1987 South Africa .

Primary Examiner—Frederick E. Waddell
Assistant Examiner—Zohreh A. Fay

[57] ABSTRACT

Substituted pyrazole, pyrrole and triazole angiotension-II receptor antagonists and pharmaceutically acceptable salts thereof are useful for treating glaucoma and ocular hypertension.

5 Claims, No Drawings

TREATMENT OF GLAUCOMA AND OCULAR HYPERTENSION WITH PYRAZOLE, PYRROLE AND TRIAZOLE ANGIOTENSIN-II RECEPTOR ANTAGONISTS

BACKGROUND OF THE INVENTION

Glaucoma is an ocular disease complex associated with an elevated pressure within the eye, i.e., elevated intraocular pressure (IOP). As a result of the elevated IOP, damage to the optic nerve, resulting in irreversible loss of visual function, may ensue. Untreated, this condition may eventually lead to blindness. Ocular hypertension, i.e., a condition of elevated IOP, without optic nerve damage or characteristic glaucomatous visual field loss, is now believed by the majority of ophthalmologists to represent the earliest phase in the onset of glaucoma. Glaucoma is among the leading causes of blindness in the U.S. today.

Drugs currently available for the control of the symptoms of glaucoma and to halt the progressive optic nerve damage are only marginally effective (Yorio (1985) *J. Ocular Pharmacol.* 1:397–422). Recently, the renin-angiotensin system (RAS) has been suggested as possibly playing a role in the maintenance of intraocular pressure, as the angiotensin-coverting enzyme (ACE) inhibitors, captopril and SCH 33861, have been shown to lower IOP in ocular normotensive rabbits (Watkins et al. (1987) *J. Ocular Pharmacol.* 3:295-307) and in humans with elevated intraocular pressures (Constad et al. (1988) *Am. J. Opthalmol.* 105:674–677) More recently, a renin inhibitor identified as Abbott-64662 was found to decrease aqueous humor formation and lower the IOP in rabbits following topical application (Stein et al. (1989) *The Pharmacologist* 31:124).

The use of certain angiotensin (AII) receptor antagonists in the treatment of elevated intraocular pressure and glaucoma has been disclosed in South African Patent Application 871653, to Schering, filed Mar. 6, 1987).

Conventional therapy for glaucoma has involved topical administration of pilocarpine and/or epinephrine, and more recently beta-blockers, such as Timolol, administered to the eye several times daily. For example, beta-blockers useful as antiglaucoma agents are disclosed in commonly-assigned U.S. patent application Ser. No. 07/285007, filed Dec. 15, 1988 (CC-0747).

SUMMARY OF INVENTION

According to the present invention there is provided a method of treating glaucoma and intraocular hypertension in a mammal comprising administering to the eye of the mammal, in an amount effective to reduce intraocular pressure, an angiotensin II antagonist compound having the formula (I):

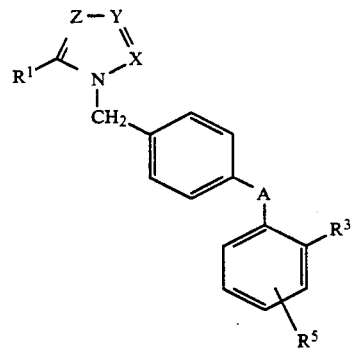

or pharmaceutically suitable salts thereof, wherein
X, Y and Z are independently N or $CR^2$ with the proviso that
1) when $R^2 \neq H$, then only one of X, Y or Z can be $CR^2$;
2) when Z=N, then Y and $X \neq CR^2$; or
3) when Y=N, then Z and $X \neq CR^2$; and
4) when X=Y=N, then $Z \neq N$;
5) when X=N, Y=Z=$CR^2$, then with respect to Y, $R^2$=$C_{3-4}$ alkyl or $C_4$ alkenyl and with respect to Z, $R^2$=H or Cl and $R^1=(CH_2)_nOR^4$ where n=1 and $R^4$=C1 alkyl, A=carbon carbon single bond, $R^3=CO_2H$ and $R^5$=H.

A is a carbon carbon single bond, CO, O, NHCO, $OCH_2$;

$R^1$ is alkyl of 2 to 6 carbon atoms, alkenyl or alkynyl of 3 to 6 carbon atoms or $(CH_2)_nOR^4$ provided that when $R^1$ is $(CH_2)nOR^4$ then $R^2$ is H, alkyl of 2 to 6 carbon atoms, alkenyl or alkynyl of 3 to 6 carbon atoms;

$R^2$ is H, alkyl of 2 to 6 carbon atoms, alkenyl or alkynyl of 3 to 6 carbon atoms;

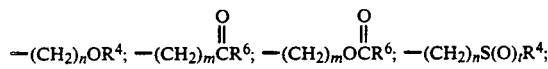

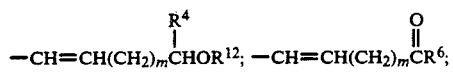

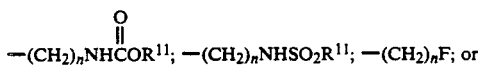

$R^3$ is

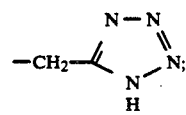

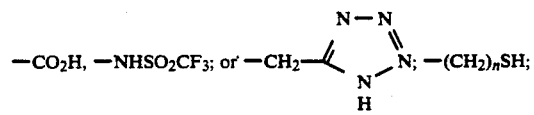

$R^4$ is H or alkyl or 1–4 carbon atoms;
$R^5$ is H, halogen, $NOX_2$, methoxy, or alkyl of 1 to 4 carbon atoms;
$R^6$ is H, alkyl of 1 to 6 carbon atoms; cycloalkyl of 3 to 6 carbon atoms, $(CH_2)_mC_6H_5$, $OR^7$ or $NR^8R^9$;

$R^7$ is H, alkyl of 1 to 5 carbon atoms, cycloalkyl of 3 to 6 carbon atoms, phenyl or benzyl;

$R^8$ and $R^9$ independently are H, alkyl of 1 to 4 carbon atoms, phenyl, benzyl or $NR^8R^9$ taken together form a ring of the formula

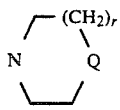

Q is $NR^{10}$, O or $CH_2$;

$R^{10}$ is H, alkyl of 1 to 4 carbon atoms or phenyl;

$R^{11}$ is alkyl of 1 to 6 carbon atoms or perfluoroalkyl of 1 to 6 carbon atoms, $(CH_2)_pC_6H_5$;

$R^{12}$ is H, alkyl of 1 to 4 carbon atoms; or acyl of 1 to 4 carbon atoms;

m is 0 to 6;
n is 1 to 6;
p is 0 to 3;
r is 0 to 1;
t is 0 to 2.

Preferred in the method of the invention are compounds of Formula (I) wherein:

A is a carbon-carbon single bond, or NHCO;

$R^1$ is alkyl, alkenyl or alkynyl each of 3 to 5 carbon atoms;

$R^2$ is H, alkyl, alkenyl or alkynyl each of 3 to 5 carbon atoms;

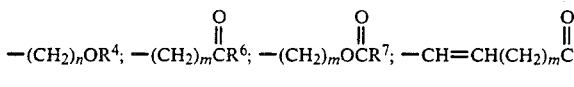

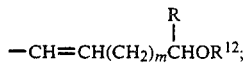

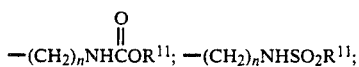

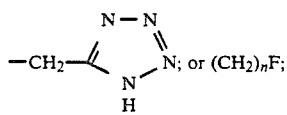

$R^3$ is

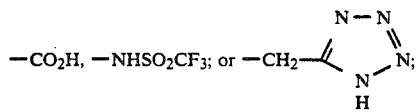

$R^3$ is $-CO_2H$, $-NHSO_2CF_3$ and
$R^4$ is H or $CH_3$;
$R^5$ is H;
$R^6$ is H, alkyl of 1 to 6 carbon atoms, $OR^7$, or $NR^8R^9$;
$R^7$ is alkyl of 1 to 6 carbon atoms;
$R^8$ and $R^9$ independently are H, alkyl of 1 to 4 carbon atoms, or taken together with the nitrogen form the ring

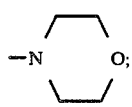

$R^{11}$ is $CF_3$, alkyl of 1 to 4 carbon atoms or phenyl;
m is 0 to 3;
n is 1 to 3;
and pharmaceutically suitable salts thereof.

More preferred in the method of the invention are compounds of Formula (I) wherein A is a carbon-carbon single bond $R^1$ is alkyl or alkenyl of 3 to 5 carbon atoms or $CH_2OR^4$; provided that when $R^1$ is $CH_2OR^4$ then $R^2$ is alkyl or alkenyl of 3 to 5 carbon atoms;

$R^2$ is alkyl or alkenyl of 3 to 5 carbon atoms, $CH_2OR^4$, $COR^6$,

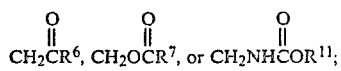

$R^6$ is H, OH, alkyl of 1 to 4 carbon atoms;
$R^7$ is alkyl of 1 to 4 carbon atoms;
and pharmaceutically acceptable salts.

Specifically preferred compounds in the method of the invention are:

3-Methoxymethyl-5-n-propyl-4-[(2'-(1H-tetrazol-5-yl)biphenyl-4-yl)methyl]-1,2,4-triazole;

3-Methoxymethyl-5-n-butyl-1-[(2'-carboxybiphenyl-4-yl)methyl]pyrazole;

5-n-Butyl-1-[(2'-carboxybiphenyl-4-yl)methyl]-1,2,3-triazole;

5-Methoxymethyl-3-n-propyl-1-[(2'-carboxybiphenyl-4-yl)methyl]pyrazole;

3-carboxy-5-n-propyl-1-[(2'-carboxybiphenyl-4-yl)methyl]pyrazole 5-n-propyl-1-[(2'-carboxybiphenyl-4-yl)methyl]pyrrole-2-carboxylic acid and pharmaceutically suitable salts thereof.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. Prefered salts of this invention for the reasons cited above include potassium, sodium, calcium and ammonium salts.

Throughout the text when an alkyl substituent is mentioned, the normal alkyl structure is meant (i.e., butyl is n-butyl) unless otherwise specified.

In the foregoing structural formula, when a substituent can be present in more than one position it can be selected independently at each occurrence. For example, if $R^4$ is present as part of both the definition of $R^3$ and A and/or B it need not be defined as the same substituent, but can be selected independently for $R^3$, A, and B.

DETAILED DESCRIPTION OF THE INVENTION

The compounds useful in this invention are described in and prepared by methods set forth in copending and commonly-assigned U.S. patent application Ser. No. 07/279,193, filed Dec. 6, 1988 (BP-6360-A) (page 13, line 1 through page 117, line 22), and corresponding European published application EPA 0 323 841, published July 12, 1989 (page 8, line 20 through page 59, line 18), the disclosures of which are hereby incorporated by reference.

The compounds of this invention are advantageously administered topically to the eye in the form of a solution, ointment, or solid insert, such as is described in U.S. Pat. No. 4,195,085. Formulations may contain the active compound, preferably in the form of a soluble acid addition salt, in amounts ranging from about 0.01% to about 10% by weight, preferably from about 0.5% to about 5% by weight. Unit dosages of the active compound can range from about 0.001 to about 5.0 mg, preferably from about 0.05 to about 2.0 mg. The dosage administered to a patient will depend upon the patient's needs and the particular compounds employed.

Carriers used in the preparations of the present invention are preferably nontoxic ophthalmologically acceptable pharmaceutical organic or inorganic compositions such as: water; mixtures of water and water-miscible solvents, such as lower alcohols; mineral oils; petroleum jellies; ethyl cellulose; polyvinylprrolidone; and other conventional carriers. In addition, the pharmaceutical preparations may also contain additional components such as emulsifying, preserving, wetting, and sterilizing agents. These include: polyethylene glycols 200, 300, 400, and 600; carbowaxes 1,000, 1,500, 4,000, 6,000, and 10,000; bacteriocidal components, such as quaternary ammonium compounds; phenylmercuric salts known to have cold sterilizing properties and which are non-injurious in use; thimerosal; methyl and propyl paraben; benzyl alcohol; phenyl ethanol; buffering ingredients such as sodium chloride, sodium borate, sodium acetates, gluconate buffers; and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotopic sodium chloride vehicles, isotonic sodium borate vehicles, and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The effect of compounds of formula I on intraocular pressure can be demonstrated in comparison to the ACE inhibitor captopril in the following Conscious Rabbit Model:

Adult New Zealand white rabbits are placed in a restrainer and their IOP measured using an Alcon Applanation Pneumatonagraph, which has both a digital output and recorder for maintaining permanent records. Three consecutive readings per eye are made (duration 10 sec. each) until a constant IOP is recorded. In some instances the peripheral ear artery is cannulated and systemic blood pressure recorded on a physiograph.

Test drugs are applied locally to one eye, either in topical form, or through intracameral administration. Measurements of IOP are made on both the treated eye and vehicle control. A dose comparable to the ocular hypotensive action found in a pilot study is selected as the starting dose and the dose is increased or decreased logarithmically and the effects on IOP is observed. Two to four log doses are tested in order to construct a log dose effect curve, which provides information on efficacy as well as potency. A time course for the drug effect is monitored by measuring the IOP of untreated animals for 60 minutes at 15 minute intervals, to obtain a baseline, and following drug addition (single dose), the IOP is measured at 30 minute intervals for six hours, or until recovery of the IOP. In addition, once a dose-effect curve is generated, the effects of agents on systemic blood pressure (BP) following topical administration are assessed by selecting the ED50 dose for testing. Thus, both changes in IOP and BP are monitored for each agent.

I claim:

1. A method of treating glaucoma or intraocular hypertension in a patient in need of such treatment which comprises topically administering to the eye, in an amount effective to reduce intraocular pressure, a compound having the formula:

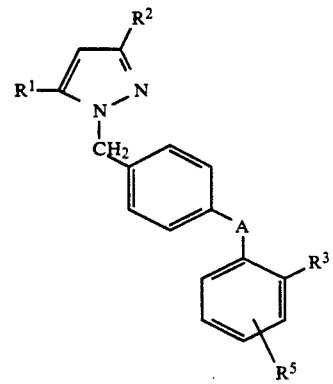

or a pharmaceutically suitable salt thereof, wherein
A is a carbon-carbon single bond, CO, O, NHCO, or OCH$_2$;
R$^1$ is alkyl of 2 to 6 carbon atoms, alkenyl or alkynyl of 3 to 6 carbon atoms, or (CH$_2$)$_n$OR$^4$ provided that when R$^1$ is (CH$_2$)$_n$OR$^4$ then R$^2$ is alkyl of 2 to 6 carbon atoms, or alkanyl or alkynyl of 3 to 6 carbon atoms;
R$^2$ is alkyl of 2 to 6 carbon atoms, alkenyl or alkynyl of 3 to 6 carbon atoms; —(CH$_2$)$_n$OR$^4$; —(CH$_2$)$_m$COR$^6$; —(CH$_2$)$_n$OCOR$^4$; or —(CH$_2$)$_n$NHCOOR$^{11}$;
R$^3$ is CO$_2$H, —NHSO$_2$CF$_3$;
R$^4$ is H or alkyl of 1–4 carbon atoms;
R$^5$ is H, halogen, NO$_2$, methoxy, or alkyl of 1 to 4 carbon atoms;
R$^6$ is H, alkyl of 1 to 6 carbon atoms; or OH
R$^{11}$ is alkyl of 1 to 6 carbon atoms or perfluoroalkyl of 1 to 6 carbon atoms or (CH$_2$)$_p$C$_6$H$_5$;
m is 0 to 6;
n is 1 to 6;
p is 0 to 3.

2. Method of claim 1 wherein the compound administered is a compound of the formula of claim 1 wherein:
A is a carbon-carbon single bond
R$^1$ is alkyl or alkenyl of 3 to 5 carbon atoms or CH$_2$OR$^4$; provided that when R$^1$ is CH$_2$OR$^4$ then R$^2$ is alkyl or alkenyl of 3 to 5 carbon atoms;
R$^2$ is alkyl or alkenyl of 3 to 5 carbon atoms, CH$_2$OR$^4$, COR$^6$, $$\overset{O}{CH_2CR^6}, \overset{O}{CH_2OCR^7}, \text{ or } \overset{O}{CH_2NHCOR^{11}};$$

R$^6$ is H, OH, alkyl of 1 to 4 carbon atoms;
or a pharmaceutically acceptable salt thereof.

3. Method of claim 2 wherein the compound is 3-Methoxymethyl-5-n-butyl-1-[(2'-carboxybiphenyl-4-yl)methyl]pyrazole or a pharmaceutically suitable salt thereof.

4. Method of claim 2 wherein the compound is 5-Methoxymethyl-3-n-propyl-1-[(2'-carboxybiphenyl-4-yl)methyl]pyrazole or a pharmaceutically suitable salt thereof.

5. Method of claim 2 wherein the compound is 3-carboxy-5-n-propyl-1-](2'-carboxybiphenyl-4-yl)methyl]-pyrazole or a pharmaceutically suitable salt thereof.

* * * * *